United States Patent [19]

Brady et al.

[11] Patent Number: 5,385,142
[45] Date of Patent: Jan. 31, 1995

[54] APNEA-RESPONSIVE VENTILATOR SYSTEM AND METHOD

[75] Inventors: Michael Brady, La Mesa; Damon Lawson, Santee, both of Calif.

[73] Assignee: Infrasonics, Inc., San Diego, Calif.

[21] Appl. No.: 870,519

[22] Filed: Apr. 17, 1992

[51] Int. Cl.⁶ .......................................... A61M 16/00
[52] U.S. Cl. ........................... 128/204.23; 128/204.22
[58] Field of Search ................. 128/204.18, 204.23, 128/204.26, 207.14, 721, 722, 725, 204.21, 204.22

[56] References Cited

U.S. PATENT DOCUMENTS

| | | | |
|---|---|---|---|
| 3,961,627 | 6/1976 | Ernst et al. | |
| 3,976,065 | 8/1976 | Durkan | 128/204.24 |
| 4,003,377 | 1/1977 | Dahl | |
| 4,072,148 | 2/1978 | Munson et al. | 128/205.11 |
| 4,281,651 | 8/1981 | Cox | 128/204.23 |
| 4,326,513 | 4/1982 | Schultz | 128/203.14 |
| 4,414,982 | 11/1983 | Durkan | 128/716 |
| 4,506,666 | 3/1985 | Durkan | 128/204.23 |
| 4,570,631 | 2/1986 | Durkan | 128/204.23 |
| 4,602,653 | 7/1986 | Ruiz-Vela et al. | 128/204.22 X |
| 4,732,159 | 3/1988 | Kraman | 128/721 |
| 4,765,340 | 8/1988 | Sakai | 128/633 |
| 4,773,411 | 9/1988 | Downs | 128/204.18 |
| 4,972,842 | 11/1990 | Korten | 128/716 |
| 5,103,814 | 4/1992 | Maher | 128/204.18 |
| 5,107,830 | 4/1992 | Younes | 128/204.18 |
| 5,107,831 | 4/1992 | Halpern | 128/204.26 |
| 5,111,827 | 5/1992 | Rantala | 128/719 |
| 5,134,890 | 8/1992 | Abrams | 128/725 X |
| 5,146,918 | 9/1992 | Kallok | 128/419 G |
| 5,148,802 | 9/1992 | Sanders et al. | 128/204.18 |
| 5,203,343 | 4/1993 | Axe et al. | 128/725 |

FOREIGN PATENT DOCUMENTS

| | | |
|---|---|---|
| 019321 | 11/1980 | European Pat. Off. |
| 324725 | 7/1989 | European Pat. Off. ....... 128/204.23 |
| 3539719 | 5/1987 | Germany ............................ 128/725 |
| 1583273 | 1/1981 | United Kingdom ........... 128/204.23 |
| 2188731 | 10/1987 | United Kingdom ................. 128/722 |
| 8202823 | 9/1982 | WIPO ................................. 128/722 |

OTHER PUBLICATIONS

Brochure of Infrasonics, Inc., "InfantStar Ventilator", 1989.
Kelvin MacDonald et., "SIMV Improves Oxygenation in Neonates", *Respiratory Care*, vol. 36, No. 11 (Nov. 1991).
Graham Bernstein et al., "Response Time of Three Patient Triggered Infant Ventilators", *Pediatric Research*, vol. 31, No. 4, part 2 (Apr. 1992).

*Primary Examiner*—Edgar S. Burr
*Assistant Examiner*—Eric P. Raciti
*Attorney, Agent, or Firm*—Gregory Garmong

[57] ABSTRACT

Patients are ventilated responsive to a temporary cessation of breathing by monitoring the spontaneous breaths of the patient and providing a series of mechanical breaths to the patient in the event that the spontaneous breaths by the patient cease. The individual breaths of the series are timed such that the rate of the breaths decreases with increasing time, to induce the patient to resume spontaneous breathing. The approach is practiced with a patient ventilator that is operable responsive to a series of commands that trigger the series of mechanical breaths, with the time between breaths gradually increasing.

15 Claims, 4 Drawing Sheets

APNEA-RESPONSIVE VENTILATOR SYSTEM AND METHOD

BACKGROUND OF THE INVENTION

This invention relates to mechanical breathing support for patients with breathing disorders, and, more particularly, to a ventilation approach that responds to temporary discontinuance of breathing by a patient.

People breathe to rid the body of carbon dioxide and other waste products of metabolism and to supply oxygen to the body for further metabolism of food. Metabolism normally continues independently of breathing, with carbon dioxide continually being produced. Each exhalation removes the carbon dioxide accumulated since the last exhalation, so that the carbon dioxide content periodically oscillates about a normal bodily level.

Apnea is a temporary cessation of the normal breathing function experienced by some persons with breathing disorders. It is often observed in prematurely born infants whose physiological and instinctive breathing function is not fully developed. Apnea is also found in adults whose ability to control breathing is curtailed by illness, bodily deterioration, or injury.

Apnea occurs when the person, whose metabolism is functioning and who has been taking spontaneous breaths in a normal manner, suddenly stops breathing. At that point, the carbon dioxide level of the blood quickly rises, because metabolism continues and the carbon dioxide is not removed from the body by breathing. Such a rise in carbon dioxide induces a normal person to take a breath, but the person subject to apnea does not. The person's body becomes increasingly poisoned by the accumulating carbon dioxide.

A person subject to apnea who is under medical care is usually monitored and an alarm is sounded when breathing stops. One conventional response to apnea is to physically stimulate the patient, as by touching, to induce the resumption of breathing. In some instances, the person undergoing apnea is already supported on a mechanical ventilator which aids breathing under a defined procedure. Some ventilators include a built-in response to apnea, which is to provide that the patient is automatically ventilated following cessation of breathing with a series of quick mechanical breaths for some fixed period of time. This rapid ventilation reduces the carbon dioxide content of the blood to well below the normal level and increases the oxygen content to more than its normal level.

Existing assisted responses to apnea are not fully satisfactory. Physical stimulation depends upon a quick response by the therapist, does not modify the blood chemistry, and is not certain to cause the resumption of breathing. A series of quick mechanical breaths alters the blood chemistry and provides immediate relief, but does not induce the resumption of breathing.

There is a need for an improved approach to responding to a condition of apnea, which both provides immediate relief to the carbon dioxide and oxygen levels of the blood and also induces the resumption of normal breathing. The present invention fulfills this need, and provides related advantages.

SUMMARY OF THE INVENTION

The present invention provides an apparatus and method for ventilating a person who is experiencing apnea. The approach of the invention automatically responds to a cessation of breathing, immediately providing assistance for correction to the blood chemistry. The apneatic person is then aided in the resumption of normal breathing. If normal breathing resumes, the assistance is discontinued. If normal breathing does not resume, the procedure is repeated as many times as necessary to induce resumption of breathing.

In accordance with the invention, a method for ventilating patients comprises the steps of monitoring the spontaneous breaths of a patient, and providing a series of mechanical breaths to the patient in the event that the spontaneous breaths by the patient cease, the individual breaths of the series being timed such that the rate of the breaths decreases with increasing time. This method is preferably accomplished using a ventilator specially adapted to respond to the apnea condition, but could be accomplished by nasal or CPAP techniques or with negative ventilation (iron lung) techniques.

In accordance with this aspect of the invention, a breathing support system comprises means for controllably supplying mechanical breaths to a patient, and means for detecting a spontaneous breath by the patient. The system includes means for initiating a series of mechanical breaths to the patient by the means for controllably supplying in the event that the means for detecting has not detected a spontaneous breath for a first period of time, and means for reducing the rate of the individual breaths in the series of mechanical breaths over a second period of time.

The present inventors have recognized that satisfactory artificial ventilation as a response to apnea must provide immediate relief to the blood chemistry, but must also induce the person's body to resume normal breathing. Physiologically, the principal impetus to breathing of persons arises from the need to rid the body of carbon dioxide. Under the conventional ventilator approach of providing the apneatic person with a quick series of mechanical breaths, the carbon dioxide level is reduced well below that which naturally produces the need to breathe. There is no need for the person's own body to breathe spontaneously, and spontaneous breathing may not resume. When the mechanical ventilation is discontinued, the carbon dioxide level may rise past the level which normally induces a breath so rapidly that the body does not have the time or inducement to initiate a breath, and the patient remains in the apneatic condition. Failure to return the patient to normal breathing is often observed when a conventional ventilator is used to respond to apnea in the normal manner.

With the present approach, a ventilator responds to the discontinuance of breathing of a patient by supplying an initial rapid series of mechanical breaths which provides immediate relief by decreasing the carbon dioxide content and increasing the oxygen content of the blood. The rate of the mechanical breaths is gradually reduced (i.e., the time between breaths is increased), so that, if the patient does not breathe spontaneously, the carbon dioxide content gradually increases toward the normal level. Initially, the gradual increase of the carbon dioxide content toward the normal level returns the body toward the normal state in a gradual manner. Further reduction of the mechanical breathing rate causes the carbon dioxide to gradually, not rapidly, increase to and above the normal level. At this point, the gradual increase in carbon dioxide content induces the body to make a spontaneous breath, so that mechanical assistance can be discontinued. Mechanical assistance can also be discontinued if breathing resumes normally at any other time. On the other hand, if normal breathing does not resume, the procedure is repeated in a further attempt to restart the breathing process in this fashion.

The present approach has the important advantages that it provides immediate relief to the person who stops breathing, but also quickly induces the person to attempt to resume the normal breathing process. It may be practiced with many existing ventilators which permit external triggering of a single breath. The present invention is of particular value in "training" premature infants to breathe properly. Other features and advantages of the invention will be apparent from the following more detailed description of the preferred invention, taken in conjunction with the accompanying drawings, which illustrate, by way of example, the principles of the invention.

DETAILED DESCRIPTION OF THE PREFERRED EMBODIMENTS

In accordance with a preferred embodiment of the invention, a ventilator system comprises a breathing ventilator that controllably supplies a mechanical breath to a patient responsive to a triggering command, and a detector that senses spontaneous breaths by the patient. The ventilator system further comprises controller means for controlling the ventilator to supply mechanical breaths to the patient in the event that the patient fails to breathe spontaneously. The controller means includes a ventilator trigger that sends the triggering command to the ventilator and a breath series controller that, upon receipt of an initiation signal, supplies a time series of commands to the ventilator trigger to produce a series of mechanical breaths to the patient. The series of commands is timed such that the rate of the individual breaths in the series of mechanical breaths decreases from an initial value to a lower value over time. The controller means further includes an initiator that supplies the initiation signal to the breath series controller in the event that the time since the last spontaneous breath as determined by the detector exceeds some preselected period of time.

Figure 1:
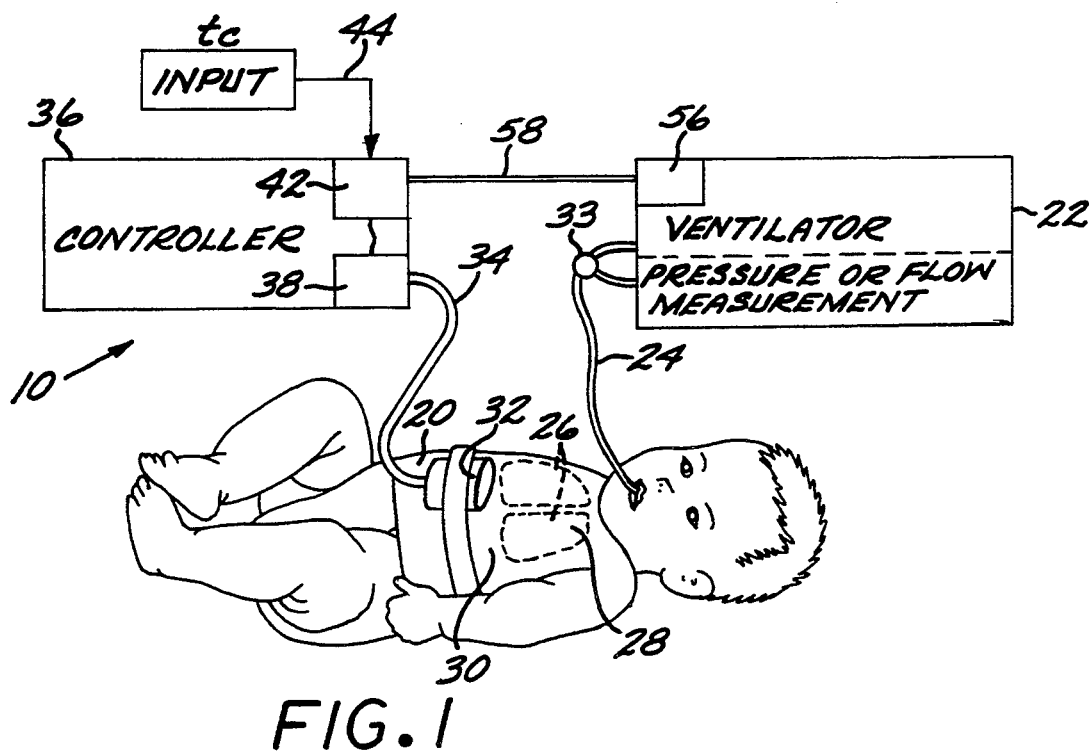
FIG. 1 is a schematic illustration of a patient supported by the mechanical ventilator of the invention.

FIG. 1 depicts a ventilator system 10 wherein a patient 20, depicted as an infant but which may be an adult, undergoes ventilation by a ventilator 22. The ventilator 22 controllably forces pressurized gas through an airway 24 into the patient's lungs 25 through its nose or mouth. Suitable ventilators that perform these functions are available commercially. A preferred ventilator 22 is a ventilator manufactured by Infrasonics, Inc., San Diego, Calif. and sold under the trademark "INFANT STAR".

When the patient 20 attempts to breathe on its own effort, termed a "spontaneous breath", its chest cavity 28 is expanded by the movement of its diaphragm 30. The movement of the chest cavity 28 and diaphragm 30 is detected by a detecting means. The preferred detecting means includes a pressure sensor 32 taped to the abdomen of the patient 20. A communication tube 34 extends from the interior of the sensor 32 to a controller 36. Within the controller is a pressure transducer 38 in pressure communication with the communication tube 34. A pressure pulse is caused in the sensor 32 by a spontaneous breath of the patient 20. The pressure pulse is transmitted through the communication tube 34 and causes the transducer 38 to generate an output signal indicative of a spontaneous breath by the patient 20. Suitable sensor 32/transducer 38 units are available from Graesby, Inc., Meridian Medical Limited, and Infrasonics, Inc.

Equivalently, the detecting means may detect a reduction in pressure or change in flow in the airway 24. A pressure detector or flow measurement device 33 may be placed into the airway 24 to detect changes indicative of a breath. The movement of the chest cavity is preferred for detecting infant breaths, as these are more frequent than adult breaths and require a faster response. Movement of the chest cavity, airway pressure changes, airway flow measurement, or other operable techniques may be satisfactory for adult applications, where the breaths are less frequent, and some infant applications.

The ventilator 22 may operate in many different modes to provide ventilation or assist the patient in its own breathing. In a typical situation involving an infant patient, the patient 20 spontaneously breathes, and the ventilator 22 is not assisting the breathing or may be supplying oxygen-enriched gas through the airway 24. That is, the ventilator is not supplanting the primary spontaneous breathing function of the patient with ventilator-initiated "machine breaths". This situation is desired, so that the infant learns to make spontaneous breaths.

In an abnormal action, the infant (or other patient) may simply stop breathing. This condition, termed "apnea", is common in prematurely born infants, whose lungs and breathing instincts have not fully developed. The present invention provides a response to the apnea that provides immediate relief and also aids the patient in resuming proper breathing.

Figure 2:
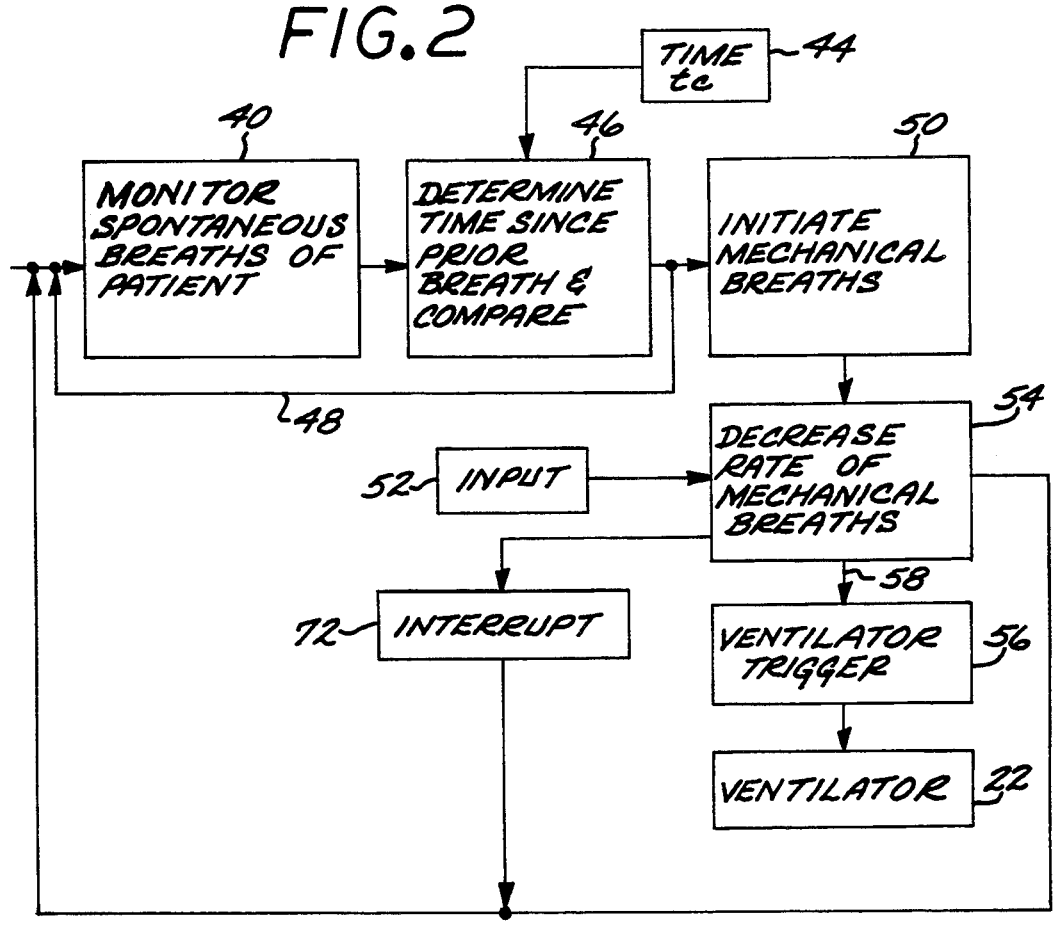
FIG. 2 is a block diagram of the method of the invention.

FIG. 2 illustrates the present response to the apnea. The controller 36 monitors the breaths of the patient 20, numeral 40, using the pressure sensor 32 and the pressure transducer 38. The output signal of the transducer 38 is provided to a breath series controller 42 within the controller 36. The breath series controller 42 determines the time since the last breath, and compares that time to a preselected time input value tc 44, see numeral 46. If the time since the last breath is less than the preselected time input value 44, the monitoring continues (return path 48). If the patient then takes another breath, the clock is reset and the comparison is made with that most recent breath.

If, on the other hand, the time since the last breath is greater than the preselected time input value 44, mechanical breathing by the ventilator 22 is initiated, numeral 50. The initial mechanical breath rate is provided as part of a set of mechanical breathing input values, numeral 52, normally established by a respiratory therapist. The rate of mechanical breathing is the number of breaths per period of time (e.g., mechanical breaths per minute) forced by the ventilator 22. The mechanical breathing continues, but the rate of mechanical breaths is thereafter reduced, numeral 54. With increasing time the mechanical breathing rate is reduced.

Figure 3:
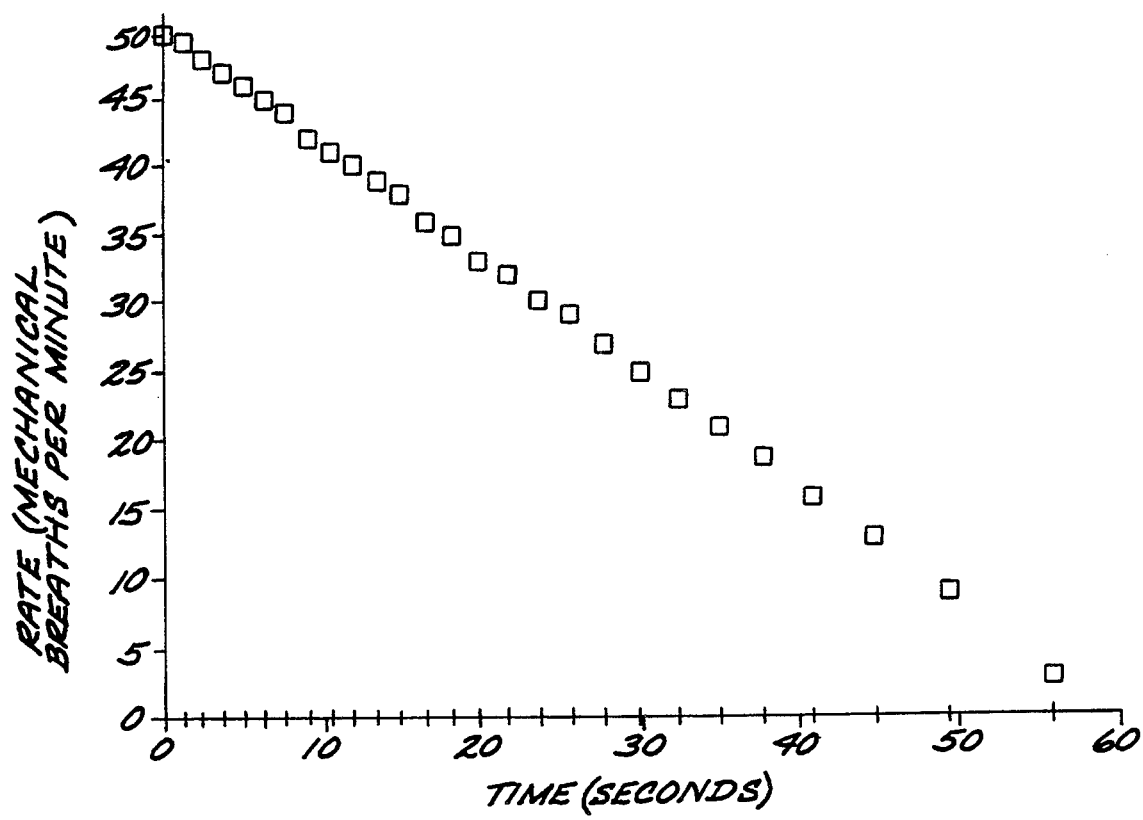
FIG. 3 is a graph of ventilator response as a function of time for a typical infant apnea, with the present approach.

FIG. 3 illustrates, by way of example, a typical mechanical breathing profile as a function of time for an infant. The initial rate of mechanical breathing, at the point of initiation, is depicted as 50 breaths per minute. The rate of mechanical breathing is thereafter reduced, linearly to zero over a one-minute period in the example. The shape of the profile, the time required to perform the profile, and the final value are all variables that are provided in the input 52 by the therapist. For example, the profile could be exponential or of other curved shape, could last more or less than one minute, and could end at some lower, but nonzero, final rate. These parameters may be selected by the respiratory therapist or built into the breath series controller, as may be appropriate. At the present time, an initial rate set by the therapist and a linearly decreasing profile to zero, over one minute, is preferred and depicted in FIG. 3.

The ventilator 22 has the capability to controllably generate a single mechanical breath upon command, when a ventilator trigger 56 is operated. (There is usually a manual button available to the respiratory therapist to operate the ventilator trigger 56, but the present apparatus operates the ventilator trigger 56 with the controller 36.) To accomplish the mechanical breathing at a decreasing rate, the breath series controller 42 determines the time at which each mechanical breath is to occur, and sends a command signal 58 to the ventilator trigger 56 at the appropriate time. The ventilator trigger 56 causes the ventilator 22 to produce a single breath.

In the preferred approach, the breath series controller 42 determines the mechanical breathing rate and the time of initiation of each mechanical breath in the following manner. As depicted in FIG. 3 and summarized in the following Table I, the first mechanical breath starts at time t=0. From the input values 52, the initial mechanical breathing rate is known. The time for such a mechanical breath to occur is the reciprocal of that value. For the case illustrated in FIG. 3 with an initial mechanical breathing rate of 50 breaths per minute, the time required for a single mechanical breath is 1.2 seconds. (This value, while very high for an adult, is typical for newly born premature infants.) The second mechanical breath is triggered at t=1.2 seconds. The mechanical breathing rate for the second mechanical breath is reduced to 49 breaths per minute, determined by interpolation (to the nearest integer, since breaths must be integral) of a linear reduction of breathing rate from 50 to 0 breaths per minute over one minute. The time required for the second breath (1/49 minute, also about 1.2 seconds) is determined. The third mechanical breath is triggered at t=1.2+1.2=2.4 seconds, and so on. As the mechanical breathing rate decreases, the time between breaths becomes longer, reaching 6.7 seconds between the twenty-sixth and the twenty-seventh (final) mechanical breath. Table I summarizes the times of initiation and rates for the case of FIG. 3. These values in this table are presented by way of example, and may vary according to experience.

TABLE I

| Breath Number | Breath Initiation Time (seconds) | Breath Rate (No./minute) |
| --- | --- | --- |
| 1 | 0 | 50 |
| 2 | 1.2 | 49 |
| 3 | 2.4 | 48 |
| 4 | 3.7 | 47 |
| 5 | 5.0 | 46 |
| 6 | 6.3 | 45 |
| 7 | 7.6 | 44 |
| 8 | 9.0 | 42 |
| 9 | 10.4 | 41 |
| 10 | 11.8 | 40 |
| 11 | 13.3 | 39 |
| 12 | 14.9 | 38 |
| 13 | 16.5 | 36 |
| 14 | 18.1 | 35 |
| 15 | 19.8 | 33 |
| 16 | 21.7 | 32 |
| 17 | 23.5 | 30 |
| 18 | 25.5 | 29 |
| 19 | 27.6 | 27 |
| 20 | 29.8 | 25 |
| 21 | 32.3 | 23 |
| 22 | 34.8 | 21 |
| 23 | 37.7 | 19 |
| 24 | 40.9 | 16 |
| 25 | 44.6 | 13 |
| 26 | 49.2 | 9 |
| 27 | 55.9 | 3 |

Figure 4:
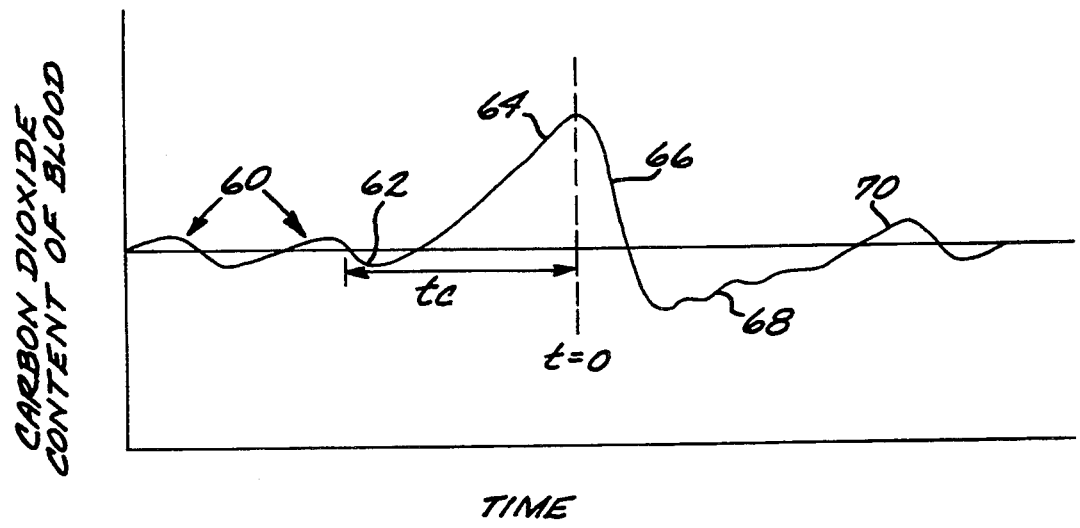
FIG. 4 is a schematic graph of blood carbon dioxide content as a function of time for the ventilator response of FIG. 3.

FIG. 4 illustrates the carbon dioxide content of the blood of the patient undergoing respiratory therapy, as a function of time. During normal respiration, numeral 60, the carbon dioxide content fluctuates about a mean normal level. When oxygen is inhaled, the carbon dioxide content of the blood increases. When breath is exhaled, the carbon dioxide content is reduced. If the patient 20 suddenly stops breathing, numeral 62, the carbon dioxide content rises far above normal levels, numeral 64. At this point, the breath series controller 42 determines that the time since the last breath has exceeded the input value tc 44, and the mechanical breathing profile depicted in FIG. 3 is initiated and continued by the process previously described. The rapid initial mechanical breathing lowers the carbon dioxide content rapidly, numeral 66. As the mechanical breathing rate slows, the production of carbon dioxide during metabolism gradually outpaces its elimination by the ever-decreasing mechanical breathing rate, and the carbon dioxide content begins to slowly rise, numeral 68.

When the carbon dioxide content of the blood reaches the normal value, the patient's own spontaneous breathing is induced to begin again, and normal breathing is resumed, numeral 70. If not, the mechanical breathing is reinitiated due to the fact that the spontaneous breathing period again exceeds tc. By this approach, the patient is given immediate relief to rapidly reduce the carbon dioxide content of the blood in the event of apnea. The decreasing mechanical breathing rate gradually induces the patient to resume spontaneous breathing.

According to one possible modification of this process, if the resumption of spontaneous breathing is detected before the profile of mechanical breaths depicted in FIG. 3 is complete, that profile is interrupted and mechanical breathing is discontinued, numeral 72 of FIG. 2, and the passive monitoring of the patient resumes, numerals 40 and 46. That is, according to this modification the mechanical breathing is stopped when the profile is complete or when the patient resumes spontaneous breathing. The inventors have not utilized this modification in their preferred approach, however, because of the possibility that mechanical breathing might be discontinued prematurely.

Figure 5:
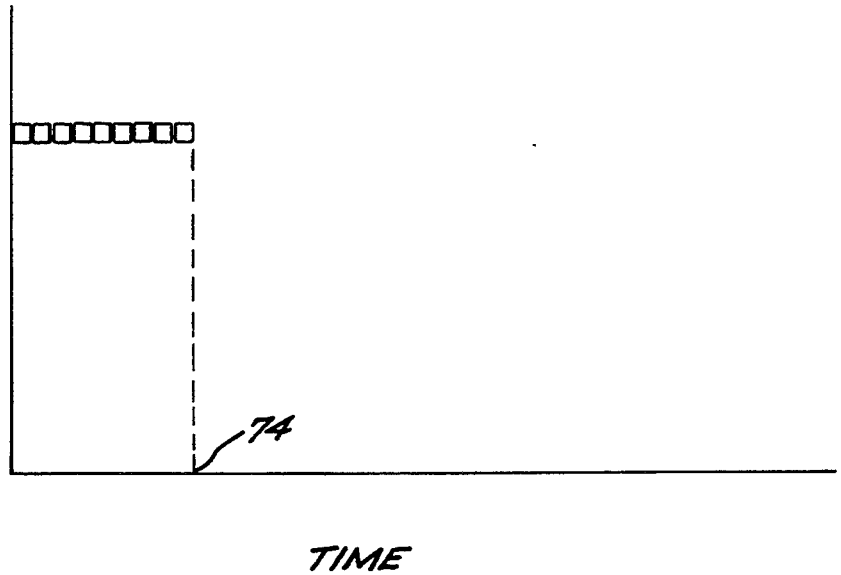
FIG. 5 is a graph of ventilator response as a function of time for a typical infant apnea, with the conventional approach.
Figure 6:
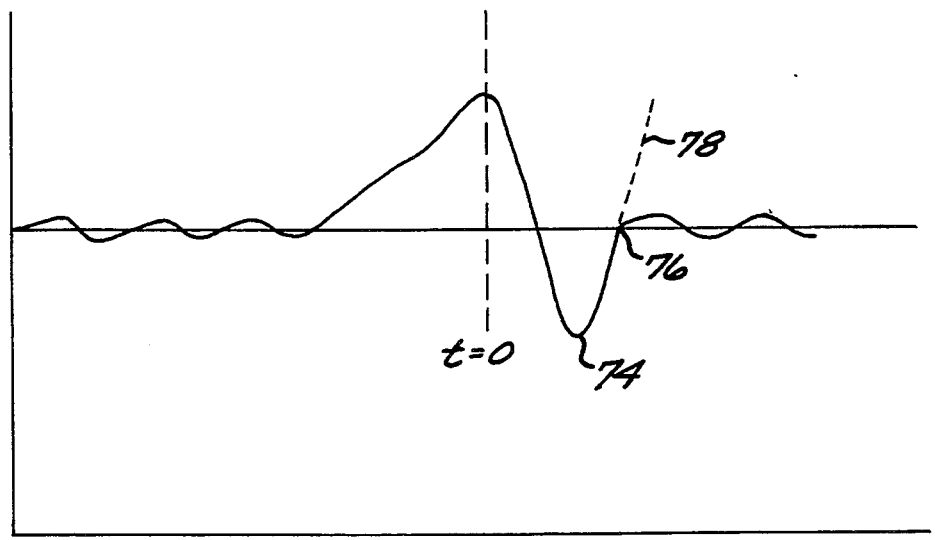
FIG. 6 is a schematic graph of blood carbon dioxide content as a function of time for the ventilator response of FIG. 5.

The present approach may-be contrasted with prior approaches. In the technique that does not utilize a ventilator, the patient is physically stimulated, as by touching or a light slap, to resume spontaneous breathing after the onset of apnea. This technique does not give the patient quick relief by lowering the carbon dioxide level, and depends upon the quick response of a nurse. FIGS. 5–6, corresponding in content to FIGS. 3–4, depict the result of the conventional ventilator response to apnea. There is a series of rapid mechanical breaths at a high rate, as shown in FIG. 5. There is immediate relief, as shown in FIG. 6, but the carbon dioxide content of the patient's blood is so reduced that the patient has no impetus to resume spontaneous breathing. After the mechanical breathing is stopped, numeral 74, the carbon dioxide content increases rapidly. It is hoped that spontaneous breathing would resume at the proper time 76, but that often does not occur. Instead, there is an overshoot in carbon dioxide content, numeral 78, because the patient's blood carbon dioxide content is not slowly raised to the normal region as in the present approach. The result is that, as is often observed, the patient has no proper combination of incentive and opportunity to resume spontaneous breathing, and then becomes dependent for life upon cycles of machine breathing. It is then difficult to wean the patient off the ventilator, and requires individual attention of the respiratory therapist. By contrast, the present approach presents the patient with carefully controlled circumstances that provide both the incentive and opportunity to resume normal breathing.

Figure 7:
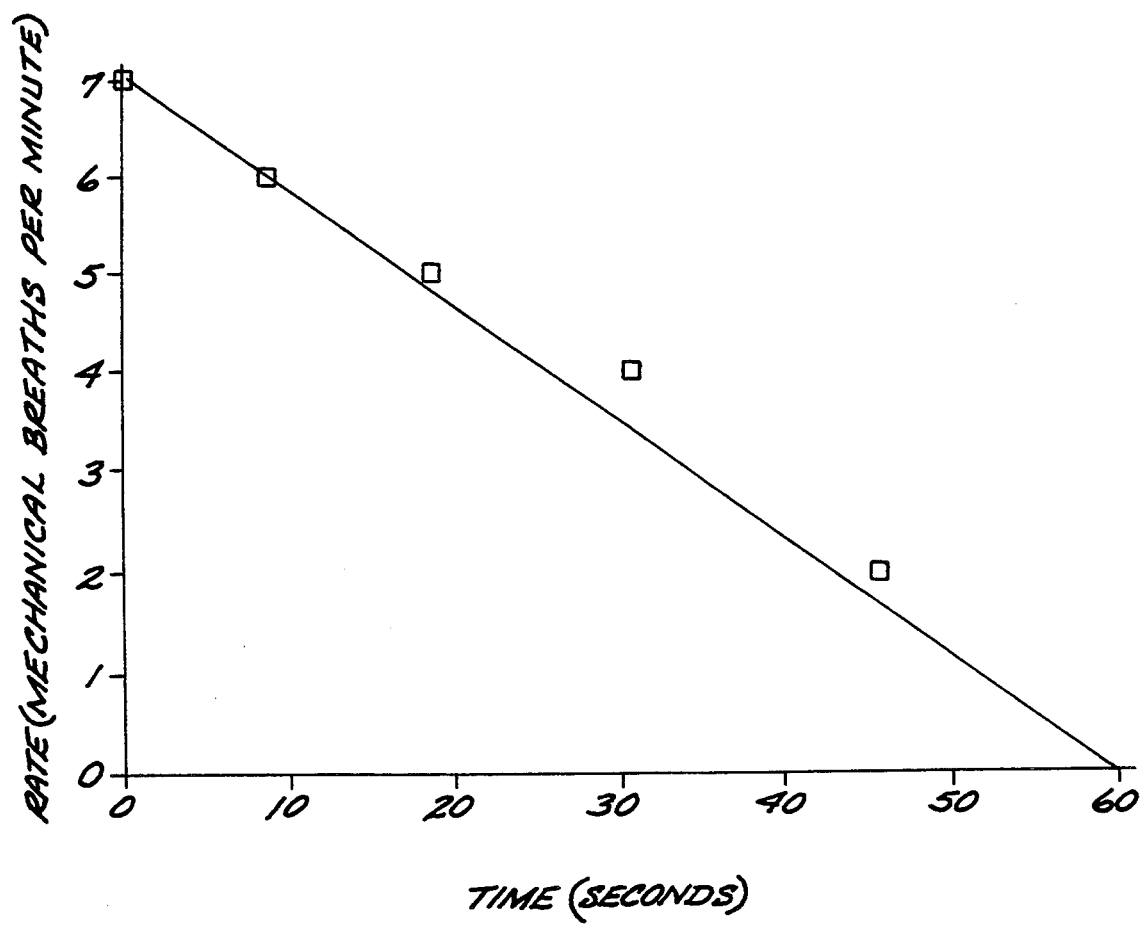
FIG. 7 is a graph of ventilator response as a function of time for a typical adult apnea.

FIG. 7 presents a breathing rate profile similar to that of FIG. 3, but designed for an adult patient with a slower normal breathing rate. Here, the initial mechanical breathing rate has been set for 7 breaths per minute. The straight line reduction is the idealized relationship. However, the actual breaths occur at the indicated square symbols, deviating from the ideal relationship slightly in some cases because they must be integers. This phenomenon is present in FIG. 3, but is much less apparent in the graph.

The present invention provides an advance in the ventilation of patients subject to apnea. The patient is provided immediate mechanical breathing relief after cessation of spontaneous breathing, but is induced to resume spontaneous breathing. Although particular embodiments of the invention have been described in detail for purposes of illustration, various modifications may be made without departing from the spirit and scope of the invention. Accordingly, the invention is not to be limited except as by the appended claims.

What is claimed is:

1. A ventilator system operable to initiate mechanical breaths if a patient has not breathed for a first period of time, and thereafter reducing the rate of mechanical breaths over a second period of time, the ventilator system comprising:
    means for controllably supplying mechanical breaths to a patient;
    means for detecting a spontaneous breath by the patient;
    means for initiating a series of mechanical breaths to the patient by the means for controllably supplying in the event that the means for detecting has not detected a spontaneous breath for the first period of time; and
    means for reducing the rate of the breaths in the series of mechanical breaths over the second period of time.

2. The ventilator system of claim 1, wherein the means for detecting includes a pressure sensor attached to the exterior of the abdomen of the patient.

3. The ventilator system of claim 1, wherein the means for supplying includes an airway leading to the patient, and the means for detecting includes means for measuring the change in pressure in the airway.

4. The ventilator system of claim 1, wherein the means for supplying includes an airway leading to the patient, and the means for detecting includes means for measuring the change in gas flow in the airway.

5. The ventilator system of claim 1, further including means for selecting an initial rate of the series of mechanical breaths.

6. The ventilator system of claim 1, further including means for selecting the first period of time.

7. The ventilator system of claim 1, wherein the means for reducing reduces the rate of the individual breaths to a preselected minimum value, and the ventilator further includes
    means for selecting the preselected minimum value.

8. The ventilator system of claim 1, further including means for selecting the second period of time.

9. A ventilator system operable to provide a series of mechanical breaths to a patient responsive to a triggering command, the ventilator system comprising:
    breathing ventilator means for supplying the series of mechanical breaths to a patient responsive to the triggering command;
    detector means for sensing spontaneous breaths by the patient;
    controller means for controlling the ventilator to supply a series of mechanical breaths to the patient in the event that the patient fails to breathe spontaneously, the controller means including
    ventilator trigger means for sending the triggering command to the ventilator,
    breath series controller means for supplying a time series of commands to the ventilator trigger to produce a series of mechanical breaths to the patient responsive to the receipt of an initiation signal, the series of commands being timed such that the rate of the breaths in the series of mechanical breaths decreases from an initial value to a lower value over time, and
    initiator means for supplying the initiation signal to the breath series controller in the event that the time since the last spontaneous breath as determined by the detector exceeds some preselected period of time.

10. The ventilator system of claim 9, wherein the detector means includes
    a transducer attached to the exterior of the abdomen of the patient that produces a pressure variation when the patient spontaneously breathes, and
    a sensor that senses pressure variations signalled from the transducer and thence a spontaneous breath by the patient.

11. The ventilator system of claim 9, wherein the ventilator includes an airway leading to the patient, and the detector means includes a pressure sensor in the airway.

12. The ventilator system of claim 9, wherein the ventilator includes an airway leading to the patient, and the detector means includes a flow sensor in the airway.

13. A ventilator system operable with a breathing ventilator that controllably supplies a mechanical breath to a patient responsive to a triggering command and a detector that senses spontaneous breaths by the patient and provides a detector signal indicative of spontaneous breaths by the patient, the ventilator system comprising controller means for controlling the ventilator to supply mechanical breaths to the patient in the event that the patient fails to breathe spontaneously, the controller means including:
- a ventilator trigger that sends the triggering command to the ventilator;
- a breath series controller that, upon receipt of an initiation signal, supplies a time series of commands to the ventilator trigger to produce a series of mechanical breaths to the patient, the series of commands being timed such that the rate of the individual Breaths in the series of mechanical breaths decreases from an initial value to a lower value over time; and
- initiator means for receiving the detector signal and for supplying the initiation signal to the breath series controller in the event that the time since the last spontaneous breath as indicated by the detector signal exceeds some preselected period of time.

14. A method for ventilating an apneic patient who fails to breathe for a first period of time and for gradually inducing the patient to resume breathing over a second period of time, comprising the steps of:
- providing a patient subject to an intermittent cessation of spontaneous breathing;
- monitoring the spontaneous breaths of the patient; and
- providing a series of mechanical breaths to the patient in response to the cessation of spontaneous breaths by the patient for the first period of time, the individual breaths of the series being timed such that the rate of the breaths decreases with increasing time over the second period of time.

15. The method of claim 14, wherein the second period of time is about one minute.

* * * * *